United States Patent [19]

Kelley

[11] Patent Number: 4,828,821

[45] Date of Patent: May 9, 1989

[54] METHOD OF INHIBITING CALCULUS FORMULATION AND IMPROVING DENTAL HYGIENE

[75] Inventor: Paul R. Kelley, Billerica, Mass.

[73] Assignee: Collaborative Research, Inc., Wilmington, Mass.

[21] Appl. No.: 899,507

[22] Filed: Aug. 22, 1986

[51] Int. Cl.[4] .............................................. A61K 7/16
[52] U.S. Cl. ..................................... 424/49; 514/835; 514/8
[58] Field of Search .......................................... 424/49

[56] References Cited

U.S. PATENT DOCUMENTS 4,663,438  5/1987  Yoshikumi ........................ 530/395

OTHER PUBLICATIONS

Yosizawa, *Tampakushitsu Kakusan Koso*, 19 (1), 27–37(1974).
*Chemical Abstracts*, vol. 81, 308 (1974), Abst. no. 61591n.
*Accepted Dental Therapeutics*, 38th ed., ADA, Chicago, Ill., 1979. pp. 343–344.
American Psychological Society, "Isolation of Calcium Oxalate Crystal Growth Inhibitor from Bat Kidney and Urine.," 1984, 0363-6127/84 F765-772.

*Primary Examiner*—Howard E. Schain
*Assistant Examiner*—F. T Moezie
*Attorney, Agent, or Firm*—Wolf, Greenfield & Sacks

[57] ABSTRACT

An inhibition of calcium salt crystal is obtained by application of acidic glycoprotein to areas to be protected from deposits or accumulations of unwanted calcium salt crystal. The acidic glycoprotein is a potent inhibitor of calculus in the body.

8 Claims, 6 Drawing Sheets

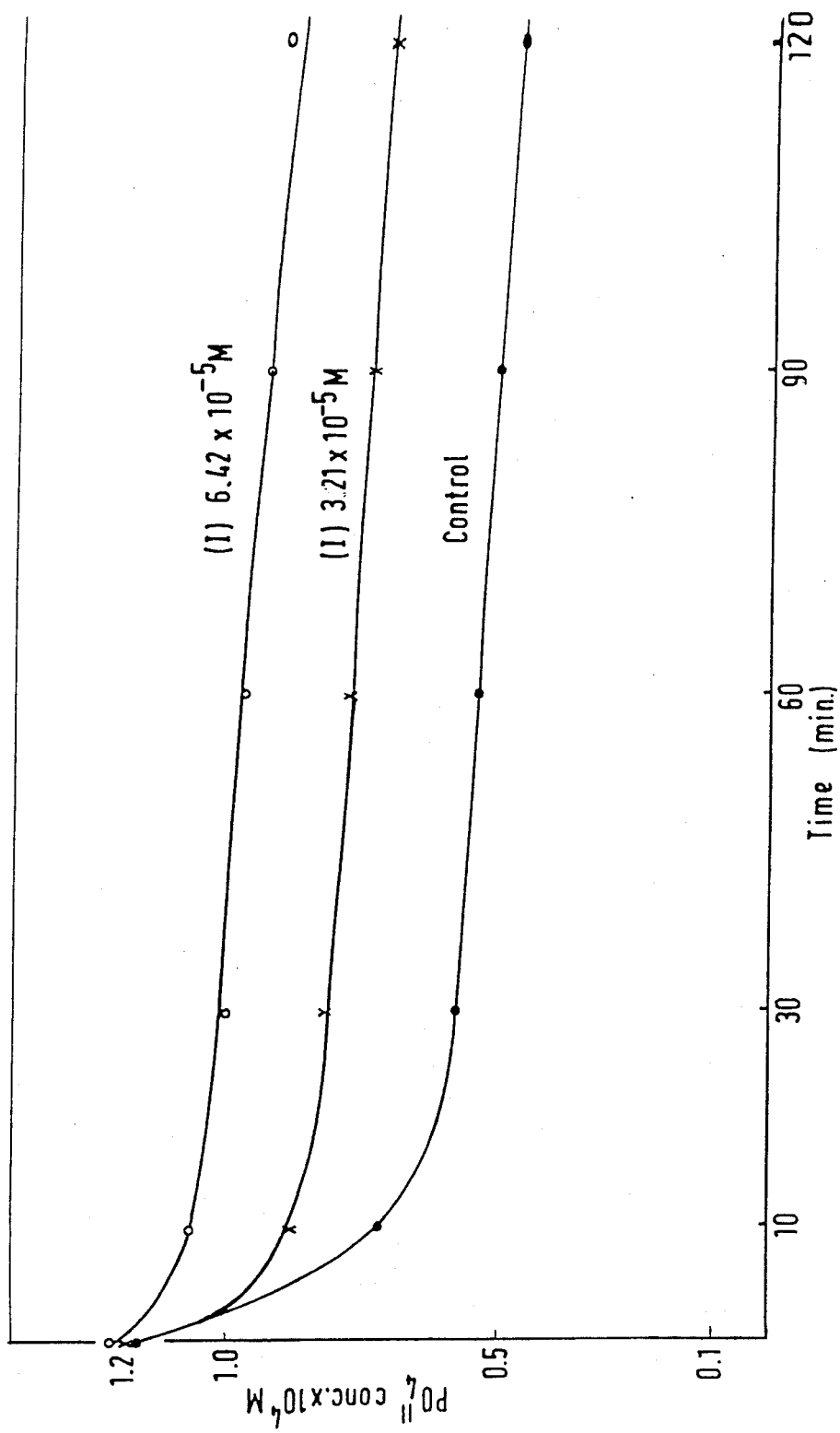

METHOD OF INHIBITING CALCULUS FORMULATION AND IMPROVING DENTAL HYGIENE

BACKGROUND OF THE INVENTION

Dental scale formed from calculus is a serious dental health problem as is the wide spread formation of dental caries in teeth. Calculus formation on teeth in the mouth can be a cosmetic problem and can cause gum and bone disease as well as aid in permitting dental caries to be formed. It has long been known that calculus comprises calcium phosphate also known as calcium hydroxyapatite crystal in certain forms. However, it has been difficult to obtain a potent material for avoiding the problems of calculus formation or aiding in the dental caries problems while still being useful in the mouth of living individuals without causing unwanted side effects.

SUMMARY OF THE INVENTION

According to the invention, a method is provided for avoiding the problems of calculus formation on unwanted areas of the body by application of an acidic glycoprotein to such areas. The acidic glycoprotein preferably has a molecular weight of from 5,000 to 100,000 and most preferably from about 10,000 to 16,000. It preferably has about 30 percent of its amino acids comprising aspartic and glutamic acid in roughly equivalent amounts and preferably has a dissociation constant of about $2 \times 10^{-9} M$ during inhibition of calcium phosphate crystal formation.

Many calcium phosphate crystal growth inhibitors are known. However, the present inhibitor has extremely good inhibition properties when used in the body as in a liquid solution topically applied to the teeth. The inhibitor is preferably obtained from conditioned media in which kidney cells are grown in culture.

BRIEF DESCRIPTION OF THE DRAWINGS

FIG. 7 is a showing of kidney stone inhibitor inhibiting calcium phosphate crystal growth.

DESCRIPTION OF PREFERRED EMBODIMENTS

Figure 1:
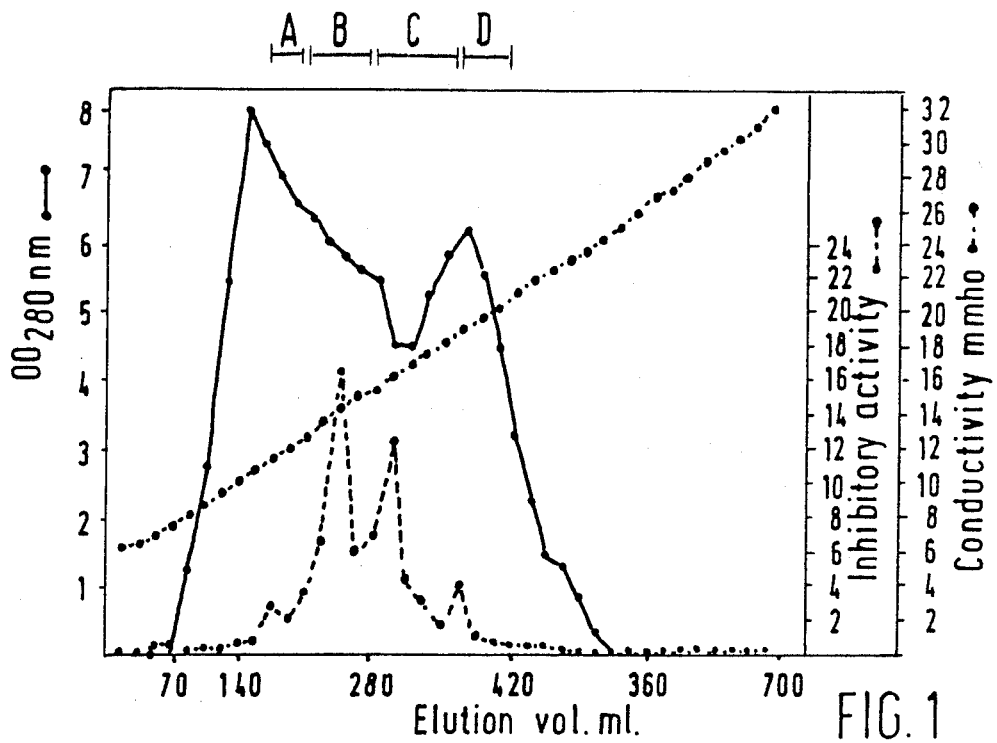
FIG. 1 shows isolation of inhibitor from human kidney tissure colture medium using colmn chromatography.

According to the method of this invention a liquid solution is preferably topically applied to the teeth to be treated. The liquid solution is preferably an aqueous solution and preferably contains from 0.001 microgram to at least 1 milligram per ml of solution when applied. The applications can be made by spraying, brushing or washing the area such as the teeth to be treated with the liquid. Preferably the liquid is maintained in contact with the teeth for a period of at least a few seconds to several minutes.

The particular anticalculus agent used is known in the art to be present in urine and obtainable by culture of kidney cells as by using conditioned tissue culture medium from a tissue kidney cell line. Suitable inhibitors are obtained from rat, human or other mammalian kidney cells. Such a calcium phosphate crystal growth inhibitor known to be useful in the present invention has the chemical composition shown in Table A below. This acidic glycoprotein can be purified from tissue culture medium as in Example 1.

TABLE A

Chemical composition of acidic glycoprotein purified from kidney tissue culture medium

| | |
|---|---|
| molecular weight | 14,000 |
| carbohydrate content | 33.4 wt % |
| axial ratio | 6/1 |
| collapsing pressure at interface of air-water (laudo film balance) | 45 dyne/cm |

| Amino acid composition (residues/molecule) | | Carbohydrate composition (residues/molecule) | |
|---|---|---|---|
| Lys | 3 | Fucose | 2 |
| His | 2 | Galactose | 9 |
| Arg | 2 | Glucose | 3 |
| Asp | 15 | Glucosamine | 3 |
| Thr | 5 | Galactosamine | 1 |
| Ser | 7 | N—Acetylneuraminic acid | 8 |
| Glu | 10 | | |
| Pro | 4 | | |
| Gly | 5 | | |
| Ala | 3 | | |
| Val | 5 | | |
| Met | 1 | | |
| Ile | 1 | | |
| Leu | 4 | | |
| Tyr | 1 | | |
| Phe | 2 | | |
| Cys | 2 | | |
| Tryp | 1 | | |

The specific inhibitor of calcium oxalate crystal growth is known and has been reported to be present in urine as reported in American Psychological Society "Isolation of Calcium Oxalate Crystal Growth Inhibitor From Rat Kindney and Urine, 1984 0363-6127/84 F765-772" a copy of which is attached hereto and incorporated by reference herein. It has now been found that this calcium oxalate inhibitor is also useful as an inhibitor of calcium phosphate in the body and acts to prevent calculus formation as on the teeth.

Generally dental scale formation and dental caries are prevented by use of the inhibitor of this invention as specifically described above. However, the inhibitor can be mixed into formulations of toothpaste or mouthwash. The specific inhibitor is a potent calcium phosphate and calcium oxalate crystal growth inhibitor.

Note that nearly 30 percent of the amino acids in the acidic glycoprotein shown in Table A are aspartic and glutamic. These strongly hydrophilic side chains are accompanied by strong hydrophobic ones. Generally the molecular weight of the inhibitor of this invention is in the range of from about 5,000 to about 100,000 and most preferably from about 10,000 to about 16,000. It preferably has about 30 percent of its amino acids comprising aspartic and glutamic acid in roughly equivalent amounts and preferably has a dissociation constant of about $2 \times 10^{-9} M$. The inhibitor which can be obtained from rat, human or other mammals, generally has a formula functionally equivalent to that of Table A obtained from human kidney culture medium in which kidney cells have been grown. The inhibitor is heat stable at 80° C. for at least five minutes and pH stable in the range of from 5 to about 9. Although the inhibitor may vary slightly when obtained from different mammalian species, its active portions are consistant and it is important that it has the characteristics noted above with the ability to substantially inhibit the growth of calcium phosphate as in the form of calcium hydroxyapatite.

Generally the calculus inhibitor of this invention is obtained from tissue culture medium in which kidney cells have been grown, or by homogenating kidneys and then extracting or by extracting from urine. The inhibitor can be absorbed onto a DEAE cellulose suspension or other cationic ion exchangers, washed with a buffer, eluted with a saline tris buffer and then desalted as by dialyzing against distilled water. The pH can be adjusted to 7.3, 0.05M salt and the solution applied to a DEAE column and eluted with a gradient of sodium chloride from, 0.05 to 0.5 Molar. Pooled fractions that have the inhibitor are obtained and can then be dialyzed against distilled water and concentrated as by lypholization after which the inhibitor can be resuspended and run over a S-200 gel exclusion column to obtain the inhibitor having the desired molecular weight.

In a specific example of this invention, crystal growth inhibitor was obtained from conditioned media in which a human kidney cell line was grown. However, the same procedure could be used to obtain the inhibitor from mammalian urine or kidney.

EXAMPLE 1

ISOLATION OF CRYSTAL GROWTH INHIBITORS FROM CONDITIONED MEDIUM

Conditioned Charity Weymouth culture medium obtained from a kidney cell line (750 ml) is dialyzed against 12 liters of deionized water for 24 hours at 4° C. with two changes. The dialysate is adjusted to 0.05M NaCl and pH 7.3, with the addition of NaCl and dilute base, respectfully. The dialysate is then mixed with 1% $NaN_3$ aqueous solution. The conductivity and inhibitory activity of every fifth fraction are determined. A typical chromatographic pattern is shown in FIG. 1. FIG. 1 shows isolation of inhibitor from human kidney tissue culture medium using DEAE-cellulose column chromatography (2×5 cm). Elution was carried out using a linear NaCl gradient from 0.05 to 0.5M in 0.05M Tris-HCl, pH 7.3 (600 ml of each solution). The fractions (3 ml/tube) were collected in test tubes containing 1 drop of 1% $NaN_3$ aqueous solution. Protein was monitored by absorption at 280 nm, and salt concentration was determined using a Radiometer conductivity meter.

Figure 2:
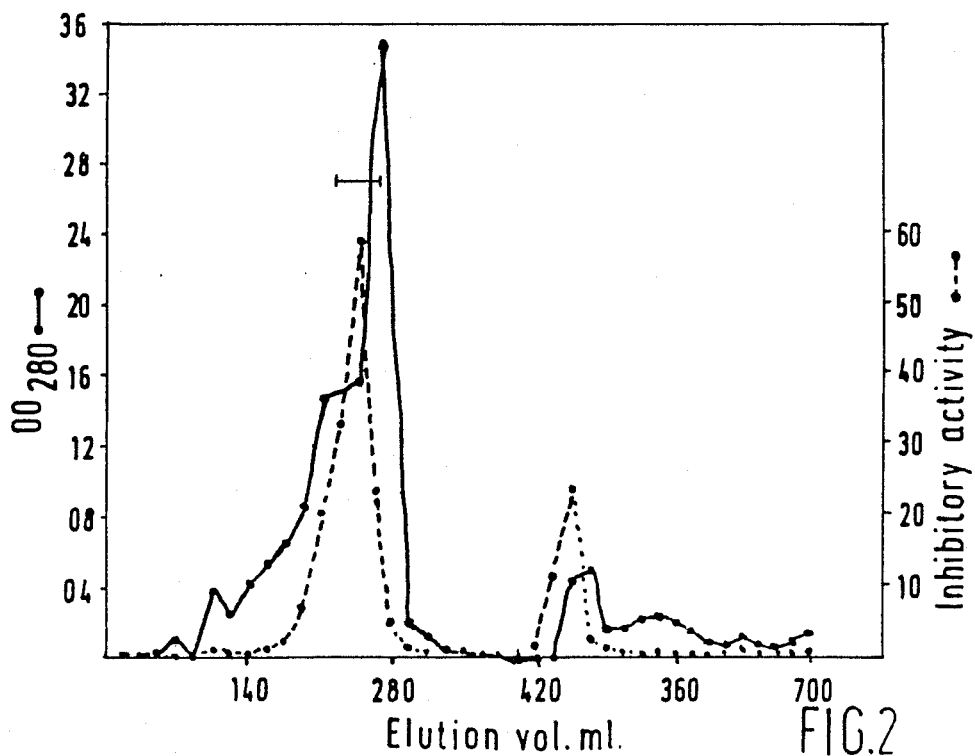
FIG. 2 shows the elution pattern of an active inhibitor fraction B.

Inhibitory activities could be separated into four fractions by conductivities; A, 11.0–12.0 mmho (0.144–0.164M NaCl); B, 12.2–15.0 mmho (0.167–0.128 M NaCl); C, 15.1–18.0 mmho (0.22–0.273M NaCl); C, 18.1–20.0 mmho (0.275–0.309M NaCl). The most active inhibitor fraction, B, is dialyzed and lyophilized to give a volume of 10 ml and then thawed. It is chromatographed on a Sephacryl S-200 column (4×113 cm) using 0.05M Tris-HCl (pH 7.3), containing a 0.2M NaCl and 0.02% $NaN_3$. The elution pattern is shown in FIG. 2.

Figure 3:
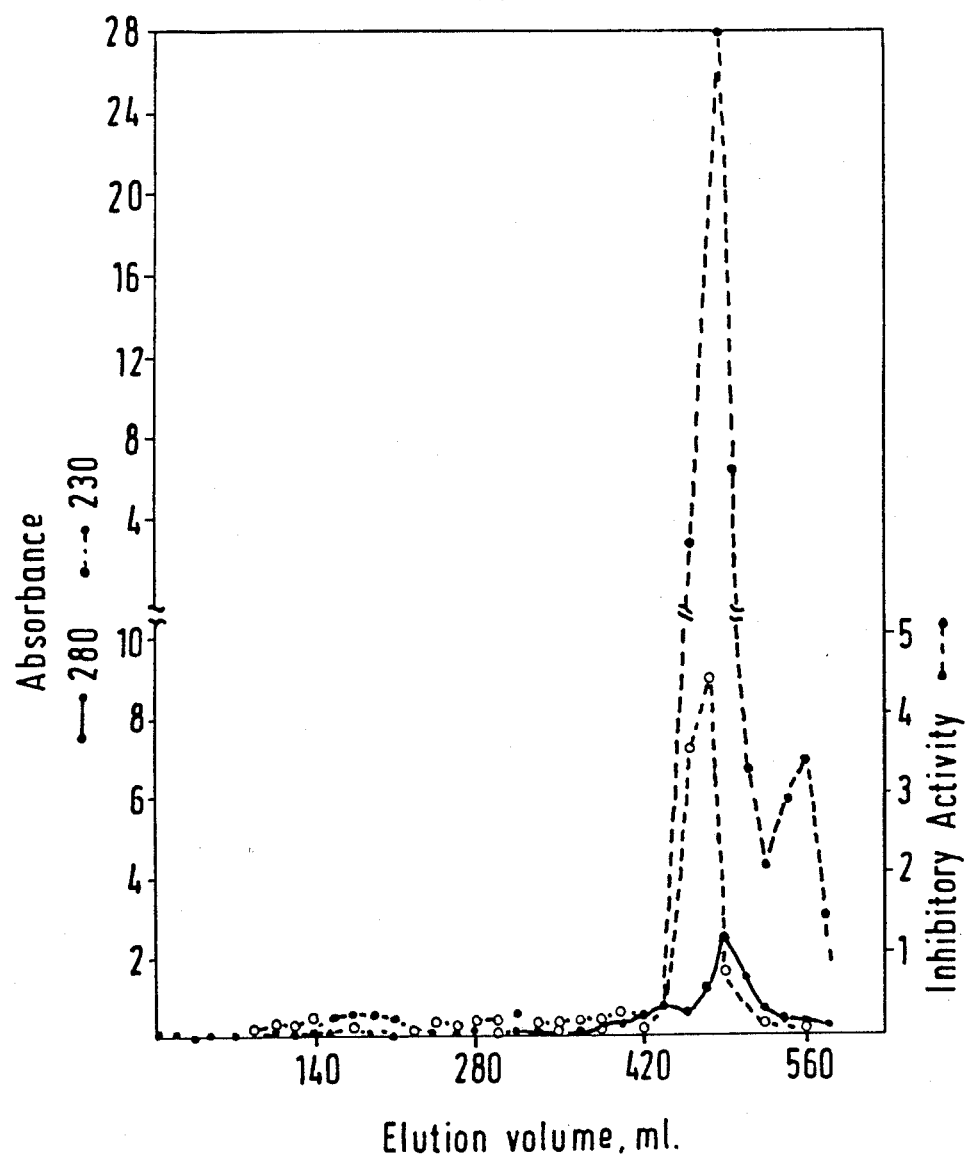
FIG. 3 shows column chromatography of a EDTA-treated inhibitor.

The major fraction is thus reduced in volume to 20 ml by lyophilization after dialysis, and adjusted to 0.1M disodium EDTA. After stirring for 12 h at 4° C. the protein solution is gel-filtered on Sephacryl S-200 (4×113 cm). The elution pattern is shown in FIG. 3. FIG. 3 shows column chromatography of the EDTA-treated inhibitor. The purified inhibitor is incubated with EDTA, then chromatographed on a column of Sephacryl S-200 (4×113 cm). The elution buffer is the same one as used previously.

The fractions under the major inhibitory peak are combined, thoroughly dialyzed against deionized water, and lyophilized. The protein recovery and purification of the inhibitor at each step is summarized in Table 2.

TABLE 2

| Purification of calcium oxalate monohydrate crystal growth inhibitor from human kidney tissue culture medium | | | | | | | |
|---|---|---|---|---|---|---|---|
| | | Protein* | | Protein | Inhibitory | Specific | Puri- |
| Step | Total volume ml | Mg/ml | Total mg | recovery % | activity units/ml | activity units/mg | fication |
| 1. Concentrated medium | 750 | 6.9 | 5178 | 100.0 | 7.4 | 1.07 | 1.0 |
| 2. Dialysis | 800 | 6.2 | 4960 | 95.8 | 6.2 | 1.00 | 0.9 |
| 3. Batch DEAE-cellulose 0.6 M NaCl eluate | 400 | 0.28 | 112 | 2.2 | 2.4 | 8.57 | 8.0 |
| 4. DEAE-cellulose column chromatography, NaCl gradient, Fraction B | 70 | 0.90 | 63 | 1.2 | 10.4 | 11.5 | 10.7 |
| 5. Sephacryl S-200 column chromatography, Fraction 1 | 125 | 0.26 | 32.5 | 0.6 | 7.85 | 30.2 | 28.2 |
| 6. Sephacryl S-200 column chromatography after EDTA treatment | 130 | 0.17 | 22.5 | 0.4 | 15.0 | 88.2 | 82.4 |

*Protein concentration determined by alkali hydrolysis

DEAE-cellulose that has been previously equilibrated with 0.05M Tris-HCl buffer - 0.05M NaCl, pH 7.3. The suspension is magnetically stirred at room temperature for 30 min., and filtered through a sintered glass filter. The inhibitors are finally eluted from the DEAE-cellulose cake with 0.05M Tris-HCl (pH 7.3) containing 0.6 NaCl by successively washing the cellulose cake with 300 and 200 ml of this buffer. The eluates are combined and dialyzed against 12 liters of deionized water for 24 h at 4° C. with two changes. After dialysis, the inhibitor solution is readjusted to pH 7.3 and 0.05M NaCl and subjected to DEAE-cellulose column chromatography (2×15 cm). The column is developed using a linear sodium chloride gradient from 0.05 to 0.5M in 0.05M Tris-HCl, pH 7.3 (600 ml of each solution). The fractions are collected in test tubes containing 1 drop of

EXAMPLE 2

In a specific example of isolation of an inhibitor suitable for use in this invention, a Waring blender, is used to blend 156 grams of rat kidneys (wet weight) to be homogenized for 3 minutes in 200 ml of 0.05Molar Tris-HCl buffer (pH 7.3) containing 0.1M NaCl. The homogenate is centrifuged at 8,000 rpm (Sorval GSA rotor) for 30 min, and the sediment is resuspended in 50 ml of the same buffer solution and recentrifuged under the same conditions. All supernatants are combined and centrifuged at 14,000 rpm (Sorval SS 34 rotor) for 30 min; 350 ml of supernatant was collected and dialyzed overnight at 4° C. against 12 liters of deionized water with one change.

The pH of the dialysate was adjusted to 7.3 and the NaCl concentration to 0.1M. The dialysate was stirred for 30 min with DEAE-cellulose, preequilibrated with 0.05M Tris-HCl containing 0.1M NaCl (pH 7.3). The suspension was filtered through a sintered glass filter, and the DEAE-cellulose cake washed with 4 liters of the equilibration buffer and then resuspended in 300 ml of 0.05M Tris-HCl containing 0.4M NaCl (pH 7.3). After 30 min of stirring, the suspension was filtered again and the filtrate was heated to 76° C. in a boiling water bath with stirring. Immediately after the solution reached 76° C., it was cooled in an ice bath and centrifuged at 8,000 rpm (Sorval GSA rotor) for 30 min. The supernatant was dialyzed overnight against 12 liters of deionized water at 4° C. with one change. The dialyzed solution was adjusted to 0.1M NaCl and applied to a column of DEAE-cellulose (2×15 cm). The protein was eluted using a linear NaCl gradient of 0.1M to 0.3M in 0.05M Tris-HCl, pH 7.3. The elute was collected in test tubes containing two drops of 1% $NaN_3$ aqueous solution.

Figure 4:
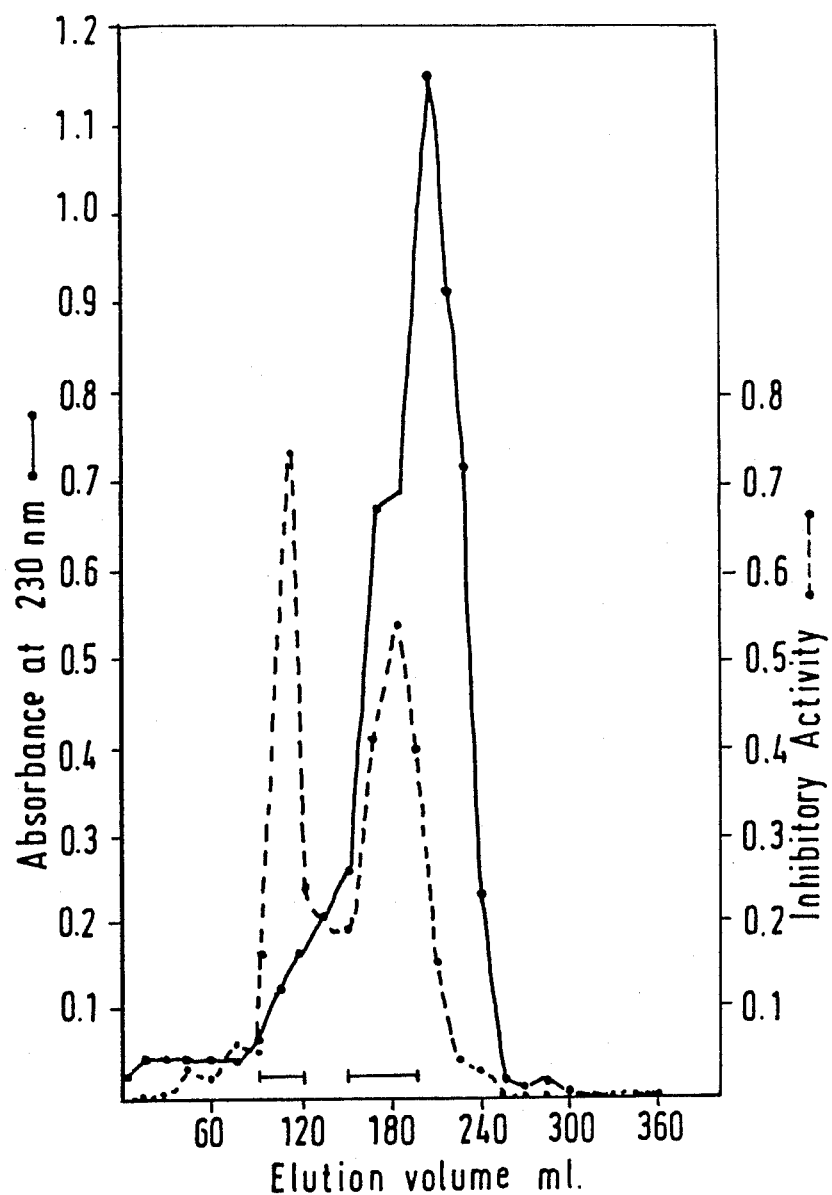
FIG. 4 shows Sephacryl S-200 column chromatography of the acidic glycoprotein useful in this invention.

The majority of the inhibitory activity was eluted at a conductivity between 15 and 20 mS/cm (equivalent NaCl concentrations of 0.22M and 0.28M). This fraction was dialyzed, lyophilized, and then passed through a column of Sephacryl S-200 (2×110 cm). Two peaks possessed inhibitory activity (FIG. 4) at apparent molecular weight of $6.5 \times 10^4$ and $1.5 \times 10^4$. FIG. 4 shows Sephacryl S-200 column chromatography.

The higher molecular weight inhibitor (apparent mol wt $6.5 \times 10^4$) was dissociated to $1.6 \times 10^4$ mol wt species after incubating with 0.05M EDTA for four days at 4° C. The molecular weight of this species was confirmed as $1.4 \times 10^4$ by HPLC with TSK-G3000 W column, and the difference of molecular weight by HPLC and S-200 chromatography was insignificant. Of the $6.5 \times 10^4$ inhibitor, 1.9 mg was recovered, with 91-fold purification, and 12.5 mg of dissociated ($1.4 \times 10^4$) inhibitor was isolated, with 58-fold purification (Table 3).

TABLE 3

Purification of calcium oxalate monohydrate crystal growth inhibitor from rat kidney homogenate

| Step | Total Volume, ml | Total Protein, mg | Specific Inhibitory Activity, units/mg | Purification |
|---|---|---|---|---|
| Supernatant of rat kidney homogenate | 350 | 24,290 | 0.33 | 1 |
| Supernatant after 0.4 M NaCl eluate heated to 76° C. | 490 | 364.6 | 14.1 | 42.7 |
| DEAE-cellulose column NaCl linear gradient | 75 | 25.67 | 21.3 | 64.5 |
| Sephacryl S-200 column | | | | |
| Peak A | 30 | 1.88 | 29.9 | 90.6 |
| Peak B | 45 | 12.5 | 19.1 | 57.9 |

EXAMPLE 3

In this example inhibitor is obtained from rat urine. Rat urine, 175 ml, is dialyzed against 12 liters of distilled water at 4° C. for 24 h with one change, adjusted to 0.1M NaCl, pH 7.3, mixed with DEAE-cellulose, and stirred for 30 min. The DEAE is filtered, and the cake is washed with 0.1M NaCl in 0.05M Tris-HCl, pH 7.3, until the wash became colorless. The inhibitor is then eluted from the DEAE-cellulose with 0.05M Tris-HCl containing 0.4M NaCl, pH 7.3.

Figure 5:
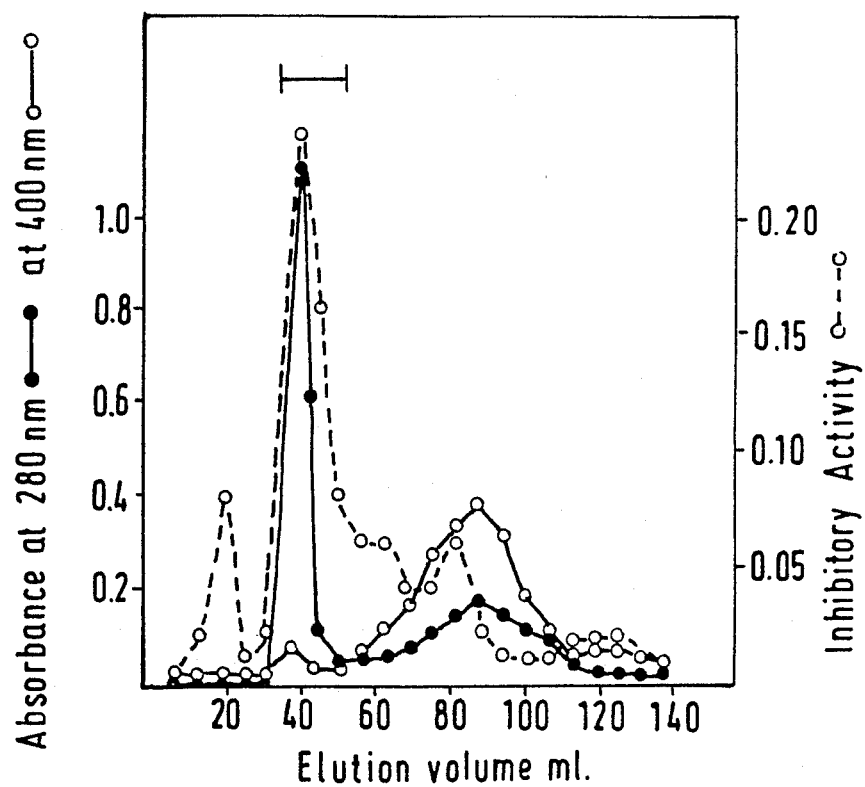
FIG. 5 shows separation of urobilirubin from rat urinary inhibitor.

The eluted inhibitor solution is dialyzed, adjusted to 0.1M NaCl, pH 7.3, and applied to a column of DEAE-cellulose. Inhibitor is eluted by linear NaCl gradient from 0.1 to 0.4M in Tris-HCl, pH 7.3. The main inhibitor peak eluted at an ionic strength of 20–22 mS/cm, similar to that of kidney homogenate inhibitor. The inhibitor was associated with pigments that were removed by passing the inhibitor through a Bio-Gel P-10 column (2×80 cm) with 50% formamide aqueous solution as a solvent (FIG. 5). FIG. 5 shows separation of urobilirubin from rat urinary inhibitor using Bio-Rad P-10 column chromatography (2×80 cm). Protein was monitored at 280 nm (●—●) and urobilirubin was detected at 400 nm (◇—◇)

Figure 6:
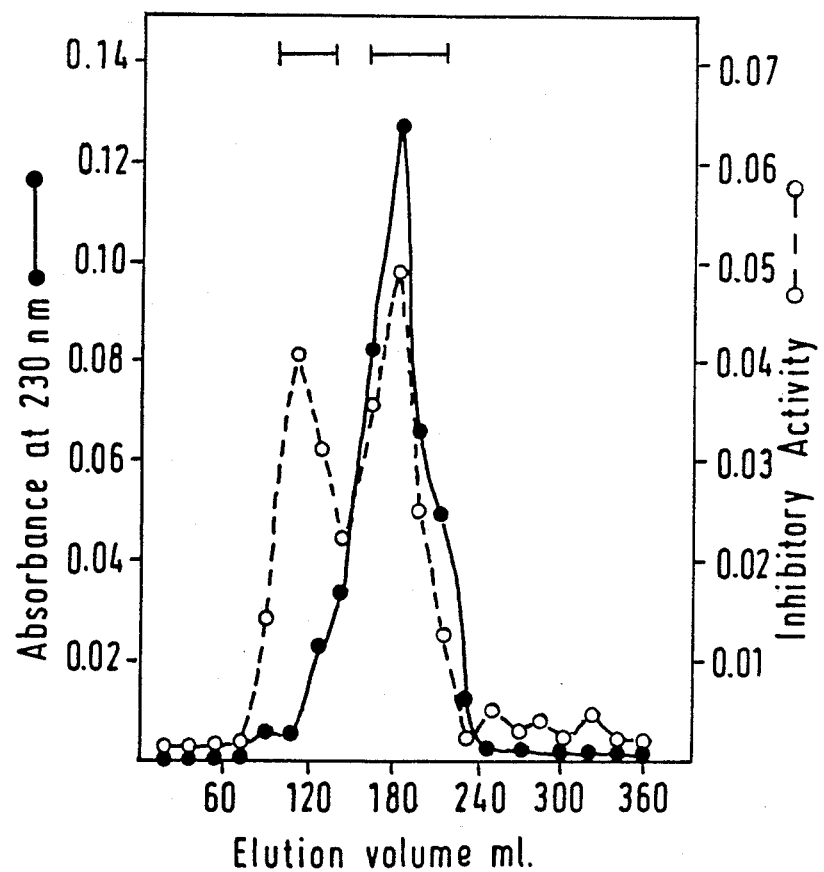

The resulting inhibitor peak was collected and applied to a Sephacryl S-200 column. Two inhibitor peaks are eluted at mol wt of 6.5 (peak A, 0.72 mg) and $1.6 \times 10_4$ (peak B, 3.6 mg) (FIG. 6). FIG. 6 shows permeation gel column chromatography of rat urinary inhibitor.

The $6.5 \times 10^4$ inhibitor dissociated to the $1.6 \times 10^4$ form, as determined by Sephacryl S-200 column chromatography after incubation with 0.05M EDTA for four days (not illustrated). The molecular weight was determined by HPLC as $1.4 \times 10^4$.

EXAMPLE 4

Kidney stone inhibitor is purified from kidney tissue culture medium (supplied from Collaborative Research) as described previously [Nakagawa et al. J. Biol. Chem. 256, 3936–3944 (1981)]. Hydroxyapatite is prepared (K. H. Muench, Procedures in Nucleic acid Research 2, 516–517) and washed with water three times then dried.

Calcium phosphate crystal growth inhibition is tested as follows:

5 ml of $CaCl_2$ ($3.9 \times 10^{-3}$M) in $5 \times 10^{-3}$M NaCl aqueous solution and 5 ml of $NaH_2PO_4$ ($2.9 \times 10^{-3}$ M) NaCl, pH 7.4, are mixed in a polyethylene tube and equilibrated at 37° with constant stirring. An aliquot of inhibitor solution is added, then the crystallization was initiated by adding 6.3 mg hydroxyapatite crystal. An aliquot of sample is withdrawn with a polyethylene syringe, filtered through a Millipore filter (0.2 um), and 100 ul of the filtrate is used for deermination of phosphate concentration by Fiske-Subbarow method [O. Lindberg and L. Ernster, Methods Biochem. Anal. 3, 1-17 (1956)].

As shown in FIG. 7, kidney stone inhibitor inhibits calcium phosphate crystal growth. The dissociation constant is estimated as $2.44 \times 10^{-9}$M. While specific examples have been shown and described, it should be understood that many variations are possible.

For example, the specific concentration of inhibitor used can vary greatly depending upon the method and area of application. Preferably solutions, gels or carriers are used to suspend the inhibitor when applied to the teeth. The inhibitor can be used in mouthwashes and other liquids as well as semi-solid materials. While the material can be merely flowed over the teeth, brushing, spraying or the like can be used.

What is claimed is:

1. A method of inhibiting calculus formation comprising applying an acidic glycoprotein to a tooth of the body, said acidic glycoprotein having a molecular weight of from about 10,000 to 16,000.

2. A method of inhibiting calculus formation comprising applying an acidic glycoprotein to a tooth of the body wherein an acidic glycoprotein material is obtained from a suspension of said glycoprotein in solution by absorbing on an ion exchange material, washing in buffer, eluting the material from said buffer, desalting, dialyzing against distilled water, adjusting in pH to about 7.3 and carrying out a gradient elution from an ion exchange column, and further comprising the step of resuspending material obtained from then last mentioned step and running said material through a gel exclusion column to obtain acid glycoprotein having a molecular weight from about 10,000 to about 16,000.

3. A method of inhibiting calculus formation comprising applying an acidic glycoprotein to a tooth of the body wherein an acidic glycoprotein material is obtained from a suspension of said glycoprotein in solution by absorbing on an ion exchange material, washing in buffer, eluting the material from said buffer, desalting, dialyzing against distilled water, adjusting in pH to about 7.3 and carrying out a gradient solution from an ion exchange column, and wherein said acidic glycoprotein has a molecular weight of from about 10,000 to about 16,000.

4. A method in accordance with the method of claim 3 wherein said acidic glycoprotein is heat stable at 80° C. for at least one minute, pH stable at a range of from about 5 to about 9 and is a calcium phosphate crystal inhibitor with a dissociation constant of about $2 \times 10^{-9}$M.

5. A method in accordance with the method of claim 4 wherein said acidic glycoprotein is derived from tissue culture media used to support the growth of kidney cells.

6. A method in accordance with the method of claim 4 wherein said acidic glycoprotein is derived from urine.

7. A method in accordance with the method of claim 4 wherein said acidic glycoprotein is derived from kidney cells.

8. A method of inhibiting calculus formation comprising applying an acidic glycoprotein to a tooth of the body wherein said acidic glycoprotein is characterized as follows:

| molecular weight | 14,000 |
| carbohydrate content | 33.4 wt % |
| axial ratio | 6/1 |
| collapsing pressure at interface of air-water (laudo film balance) | 45 dyne/cm |

| Amino acid composition (residues/molecule) | | Carbohydrate composition (residues/molecule) | |
| --- | --- | --- | --- |
| Lys | 3 | Fucose | 2 |
| His | 2 | Galactose | 9 |
| Arg | 2 | Glucose | 3 |
| Asp | 15 | Glucosamine | 3 |
| Thr | 5 | Galactosamine | 1 |
| Ser | 7 | N—Acetylneuraminic acid | 8 |
| Glu | 10 | | |
| Pro | 4 | | |
| Gly | 5 | | |
| Ala | 3 | | |
| Val | 5 | | |
| Met | 1 | | |
| Ile | 1 | | |
| Leu | 4 | | |
| Tyr | 1 | | |
| Phe | 2 | | |
| Cys | 2 | | |
| Tryp | 1 | | |

* * * * *